US006828472B1

(12) United States Patent
Sakaguchi (10) Patent No.: US 6,828,472 B1
(45) Date of Patent: Dec. 7, 2004

(54) INBRED MOUSE STRAIN SELECTED FOR AUTOIMMUNE ARTHRITIS

(75) Inventor: Shimon Sakaguchi, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/284,114

(22) PCT Filed: Oct. 7, 1997

(86) PCT No.: PCT/JP97/03591

§ 371 (c)(1),
(2), (4) Date: Apr. 7, 1999

(87) PCT Pub. No.: WO98/15173

PCT Pub. Date: Apr. 16, 1998

(30) Foreign Application Priority Data

Oct. 8, 1996 (JP) .............................................. 8-267126

(51) Int. Cl.⁷ ............................................ A01K 67/027
(52) U.S. Cl. ...................................................... 800/18
(58) Field of Search ............................. 800/18, 8, 9, 3, 800/21, 22; 435/4

(56) References Cited

U.S. PATENT DOCUMENTS 4,950,741 A * 8/1990 Yamanaka et al. .......... 530/387

OTHER PUBLICATIONS

Nakamura, K. et al. Spontaneous Degenerative Polyarthritis in Male New Zealand Black/KN Mice. Arthritis and Rheumatism 34(2):171–179, Feb. 1991.*

Hang, L. et al. A Spontaneous Rheumatoid Arthritis–Like Disease in MRL/1 Mice. Journal of Experimental Medicine 155:1690–1701, Jun. 1982.*

Bouvet, J.–P. et al. Spontaneous Rheumatoid–Like Arthritis in a Line of Mice Sensitive to Collagen–Induced Arthritis. Arthritis and Rheumatism 33(11): 1716–1722, Nov. 1990.*

Nordling, C. et al. Characterization of a Spontaneously Occurring Arthritis in Male DBA/1 Mice. Arthritis and Rheumatism 35(6):717–722, Jun. 1992.*

Kalyani et al., Neuoepithelial Stem Cells from the Embryonic Spinal Cord: Isolation, Characterization, and Clonal Analysis, 1997, Developmental Biology, vol. 186, pp. 202–223.*

The Merck Veterinary Manual. Fraser, C. et al. (Ed.) Merck & Co., Inc. Rahway, New Jersey, Feb. 1991.*

Hang, L., et al., "A Spontaneous Rheumatoid Arthritis–Like Disease in MRL/1 Mice", J. Exp. Med., vol. 155, p. 1690–1701 (1982).

Bouvet J–P., et al., "Spontaneous Rheumatoid–Like Arthritis in a Line of Mice Sensitive to Collagen–Induced Arthritis", Arthritis Rheum., vol. 33, p. 1716–1722 (1990).

Nordling, C., et al., "Characterization of a Spontaneously Occurring Arthritis in Male DBA/1 Mice" Arthritis Rheum., vol. 35, p. 717–722 (1992).

* cited by examiner

Primary Examiner—Michael C. Wilson
(74) Attorney, Agent, or Firm—Fish & Richarson P.C.

(57) ABSTRACT

The present invention provides a mouse model with natural onset of morbid conditions strikingly similar to those of rheumatoid arthritis in humans. This mouse strain can be utilized as an animal model of rheumatoid arthritis.

1 Claim, 10 Drawing Sheets

INBRED MOUSE STRAIN SELECTED FOR AUTOIMMUNE ARTHRITIS

RELATED APPLICATIONS

This application is a national phase application under 37 CPR §371 of international application no. PCT/JP97/03591, which claims priority to Japanese patent application no. 267126/1996, filed Oct. 8, 1996. Each of the aforementioned applications are explicitly incorporated herein by reference in their entirety and for all purposes.

TECHNICAL FIELD

The present invention relates to a mouse model with natural onset of morbid conditions strikingly similar to those of rheumatoid arthritis developing in humans. This strain of mice is useful as an animal model of rheumatoid arthritis.

BACKGROUND ART

Among autoimmune diseases, rheumatoid arthritis is the most frequent disease; for example, the number of patients with this disease in the US is estimated to be 6.5 millions. The cause and pathogenetic mechanism of this disease are largely unknown at present.

For elucidation of the cause and mechanism of diseases of unknown etiology, animal models are useful, especially when they naturally develop the diseases clinically and pathologically similar to the human counterparts. For example, the NOD strain of mice develop insulin-dependent diabetes mellitus, which is an autoimmune disease like rheumatoid arthritis (Makino, S. et al. Exp. Animals (Tokyo) 29, 1-13, 1980). NZB and NZW mice are used widely as a model for systemic lupus erythematosus (SLE) (Andrews, B. S. et al., J. Exp. Med. 148, 1198-1215, 1978). These animals have greatly contributed to the elucidation of the cause and mechanism of respective diseases.

Some animals showing similar morbid conditions to those of rheumatoid arthritis in humans are also known. For example, MRLlpr/lpr mice show natural onset of arthritis mainly in the leg joints (Hang, L. et al., J. Exp. Med. 155:1690, 1982). However, the arthritis in this strain is generally mild, and the maintenance of the strain for a prolonged period is difficult because of abnormal proliferation of lymphocytes in the lymph nodes and spleen, hampering the wide use of the strain as a model of arthritis. Collagen arthritis can be induced in mice by immunizing with type II collagen, which is abundant in joints, along with strong adjuvant (Stuart, J. M. et al., Annual Rev. Immunol. 2;199, 1984). Adjuvant arthritis can also be induced in rats by immunizing with dead tubercule bacilli (Taurog, J. D. et Mu al., Cell Immunol. 75:271, 1983). Although these models show morbid conditions similar to those of rheumatoid arthritis, the relationship of human rheumatoid arthritis to the abnormality of type II collagen or to the infection with tubercule bacilli is not proven. Accordingly, the findings obtained by utilizing these model animals cannot necessarily be extrapolated to humans, and it is contenions whether these animals can be used as suitable models of human rheumatoid arthritis.

PROBLEM TO BE SOLVED BY THE INVENTION

An animal model with immunopathological characteristics of rheumatoid arthritis, is necessary for development of effective therapies for rheumatoid arthritis in humans. The present invention meets such a requirement, and the object of the invention is to provide a mouse model with natural onset of morbid conditions strikingly similar to those of rheumatoid arthritis in humans.

A deposit of the SKG strain has been made with and accepted by the International Patent Organism Depositary, National Institute of Advanced Industrial Science and Technology, located at AIST Tsukuba Central 6, 1-1, Higashi 1-Chome, Tsukuba-shi, Ibaraki-ken 305-8566, Japan, on Nov. 6, 2001. The Accession Number is FERM BP-7790.

DISCLOSURE OF THE INVENTION

As a result of his extensive study for solving the problems described above, the present inventor found a mouse with joint swelling among a normal BALB/c colony, and from this finding, attained the present invention. Hence, the present invention is a mouse strain having the character of natural onset of autoimmune arthritis. This mouse strain was designated as the SKG strain.

Hereinafter, the present invention is described in detail.

The mouse of the invention, which was designated as the SKG strain, possesses the character of natural onset of autoimmune arthritis. Although the time of onset of autoimmune arthritis varies among individual mice, the onset of the arthritis is usually about 3 to 4 months after birth. As described in the "BACKGROUND ART" above, MRL-lpr/lpr mice also show natural onset of arthritis. However, the mouse of the invention and the MRL strain are different in their morbid conditions. For example, the arthritis in the MRL strain is generally localized to the joints of the hind legs, and even after progressing chronically, does not lead to joint stiffening, while the arthritis in the mouse of the invention develops in the joints of the forelegs and hind legs, and chronically progressing to joint stiffening. Furthermore, the mouse of the invention does not show the abnormal proliferation of lymphocytes or the SLE-like lesions observed in the MRL strain.

Figure 9:
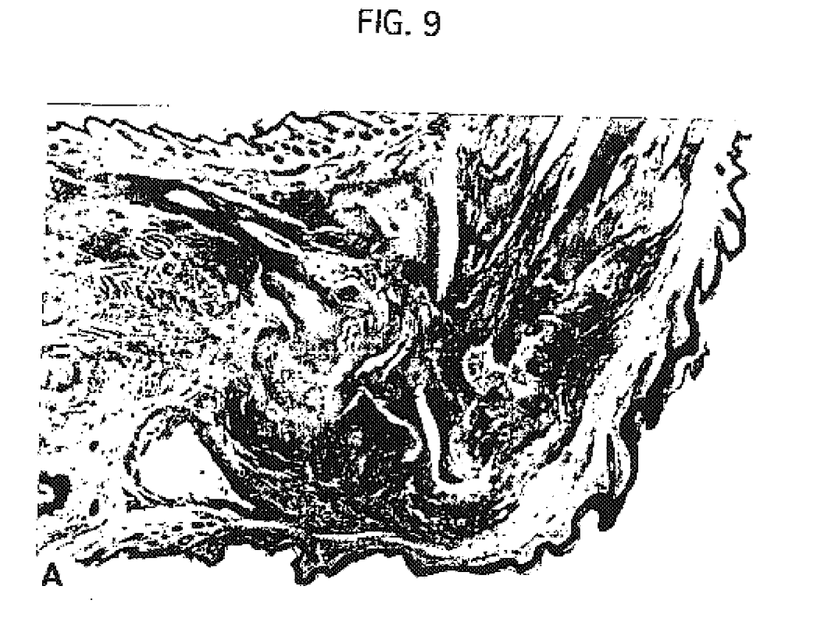
FIG. 9 is a microscopic photograph (magnification: ×40) of a section of the joint tissue prepared from a SKG mouse having developed arthritis.
Figure 11:
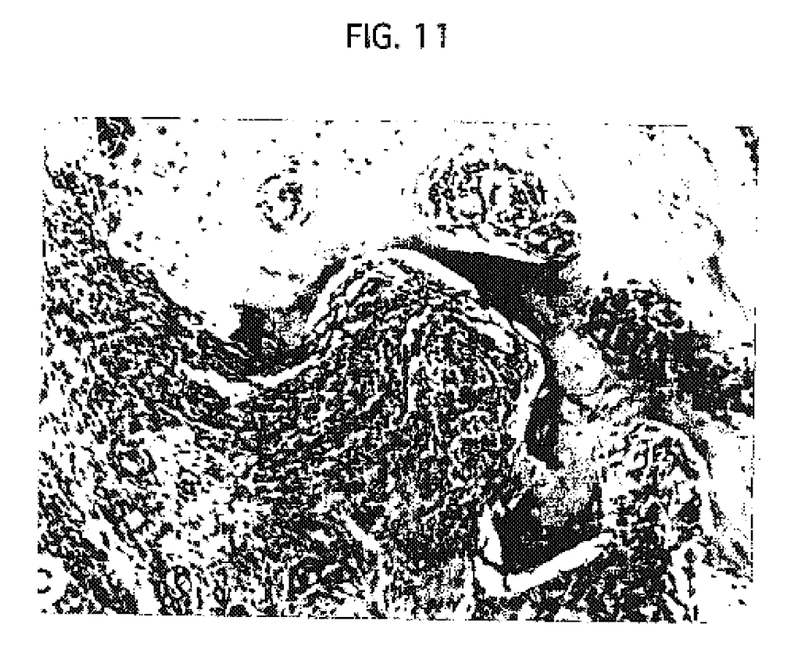
FIG. 11 is a microscopic photograph (magnification: ×400) of a section of the joint tissue prepared from a SKG mouse having developed arthritis.

The autoimmune arthritis observed in the mouse of the invention is strikingly similar to human rheumatoid arthritis in morbid conditions. Specifically, there are the following similarities therebetween:

1) It pathohistologically resembles human rheumatoid arthritis in its chronic progression from the appearance of pannus to the inflammatory destruction of joint cartilage and bone accompanied by lymphocyte infiltration (FIGS. 9 and 11).

2) Clinically, it resembles human rheumatoid arthritis in that the small and large joints of the forelegs and hind legs are affected symmetrically, and in that the lesions chronically progress and finally lead to joint stiffening (FIGS. 1, 3, 5 and 7).

Figure 14:
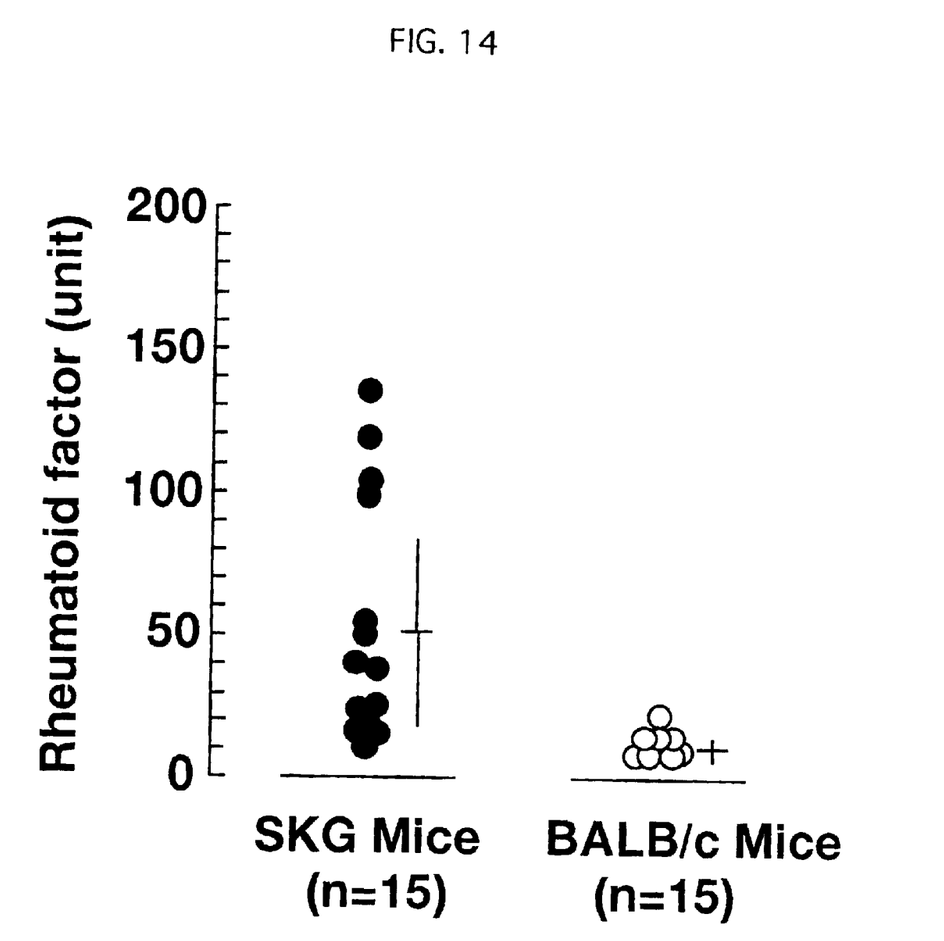
FIG. 14 is a graph showing the titer of rheumatoid factor in SKG mice at 56 months of age.
Figure 15:
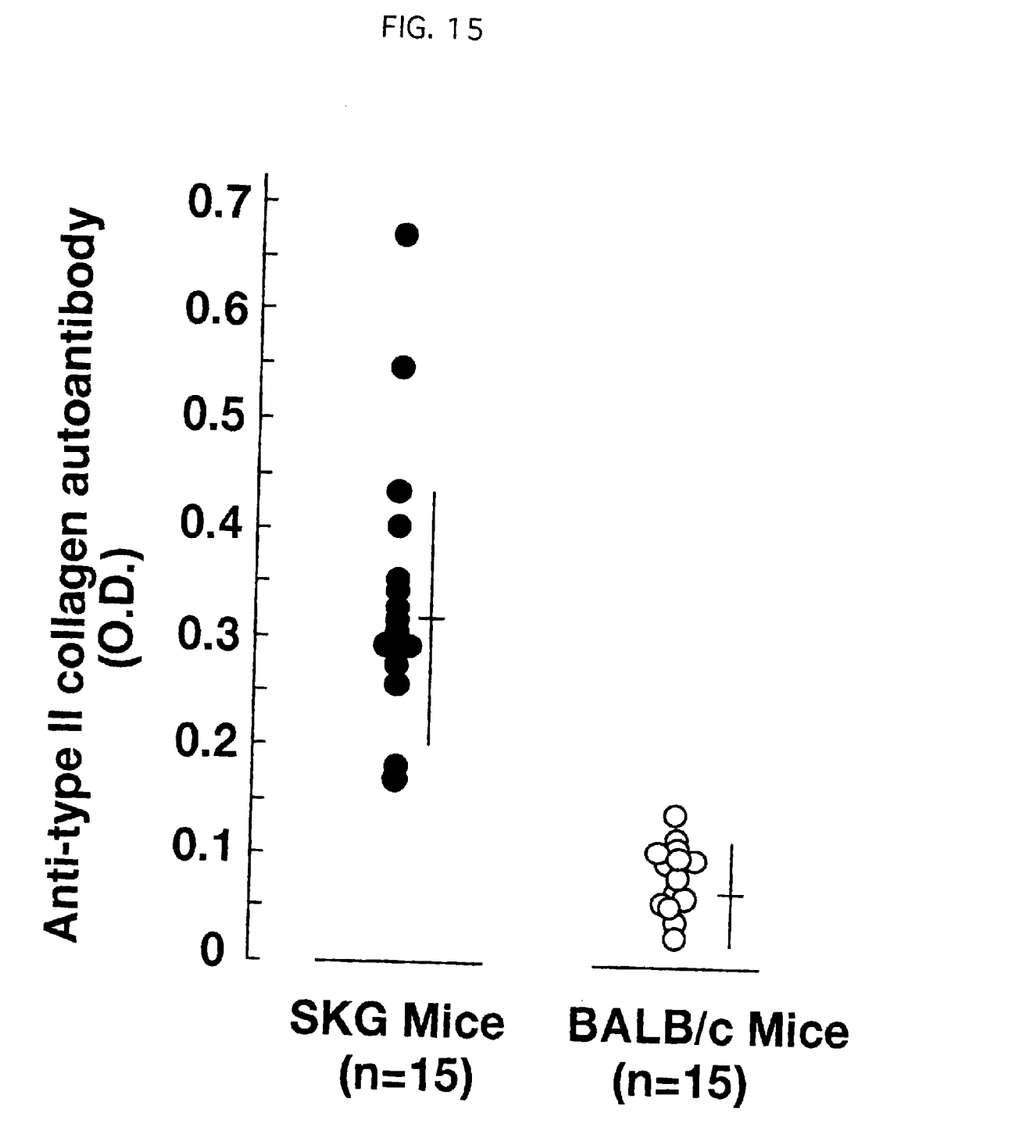
FIG. 15 is a graph showing the titer of autoantibody against type II collagen in SKG mice at 56 months of age.
Figure 16:
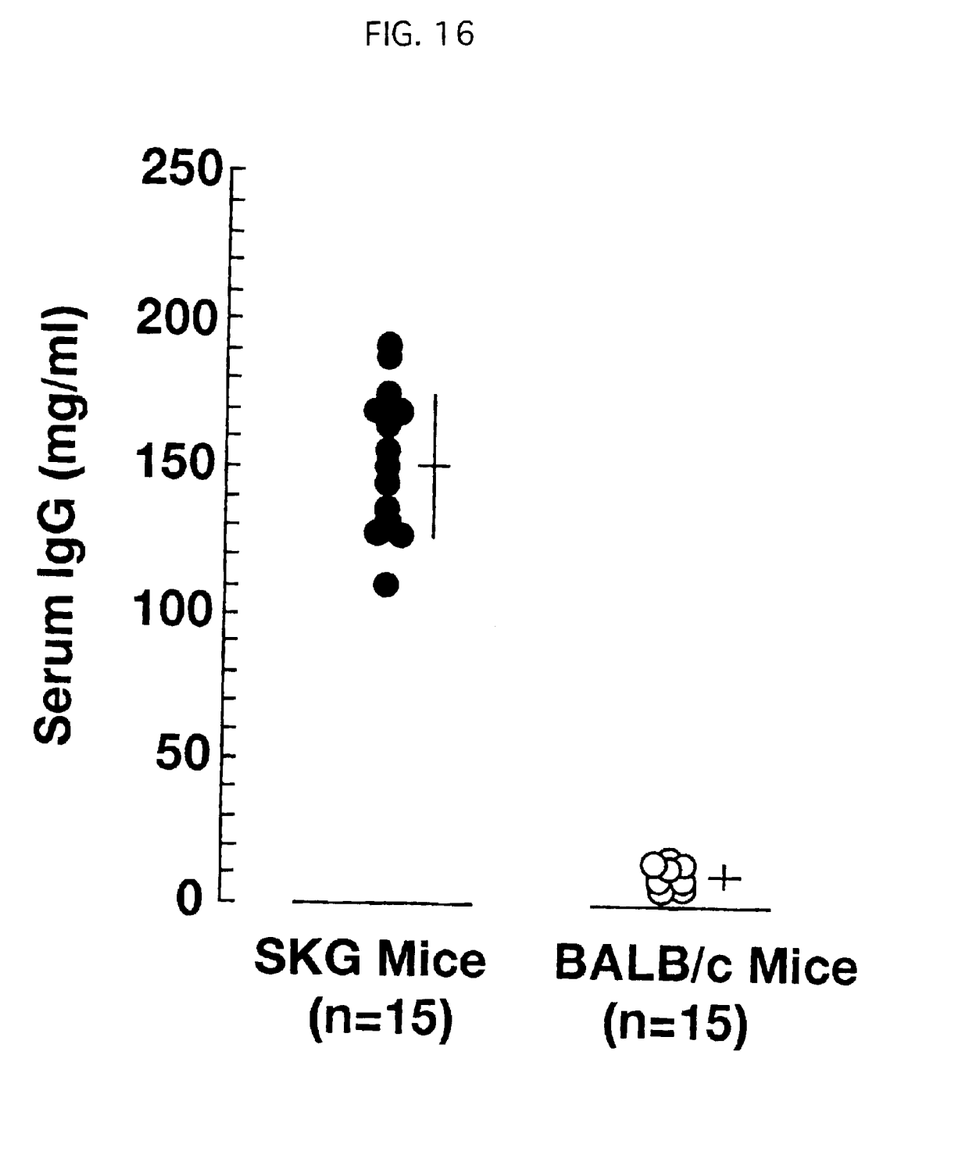
FIG. 16 is a graph showing serum igg levels in skg mice at 56 months of age.

3) It resembles human rheumatoid arthritis in that rheumatoid factor, autoantibody against type II collagen specific for joints, and hypergammaglobulinemia develops highly frequently in the mouse of invention (FIGS. 14, 15 and 16).

From these similarities, the mouse of the invention can be used as a good model of human rheumatoid arthritis. The mouse of the invention can be produced by mating between SKG strain of mice or by mating them with other suitable strains of mice and selecting the obtained mice for those having the characters described above. The applicant will distribute the SKG strain of mice in accordance with the stipulation of Article 27-3, Item 1, of the Japanese Patent Law Enforcement Regulations.

EXAMPLES

Example 1

In 1993, a female mouse with joint swelling was found in an inventor's BALB/c colony (purchased in 1992 from Nippon SLC) in the Institute for Physical and Chemical Research. This joint swelling was assumed to be due to a genetic mutation; and this mutant strain was designated as SKG. The following experiments were conducted to examine the properties of its gene.

The SKG mouse having developed arthritis was mated with a BALB/c mouse (originally purchased from Nippon SLC). As the result of this mating, 12 mice were obtained, among which 4 mice (3 females and X male) showed joint swelling (the incidence of arthritis: 33%). One mouse was arbitrarily selected from the mice having joint swelling and mated again with a BALB/c mouse in a mouse colony (originally purchased from Nippon SLC) maintained in the inventor's laboratory. As the result of this mating, 15 mice were obtained, among which 6 mice (4 females and 2 males)had joint swelling (the incidence of arthritis: 40%). One mouse was arbitrarily selected from the mice having joint swelling and mated again with another mouse in the above-described BALB/c colony. As the result, 28 mice were obtained, among which 10 mice had joint swelling (the incidence of arthritis: 35%). As the result of the above matings through 3 generations, arthritis developed at the incidence of 30 to 40% in both male and female mice when mated with BALB/c mice in the inventor's colony.

It was initially considered that the BALB/c mice used in the mating experiments described above were normal and had not developed arthritis. It was also considered from the above results that the gene causing the natural onset of the autoimmune arthritis showed autosomal inheritance dominant. However, in later experiments, the BALB/c mice considered normal and apparently free of swelling in large joints (e.g. leg joints), were found by detailed observation for a long period (6 months or more)to have joint swelling in small joints of the fingers. Furthermore, although the incidence of arthritis in large joints was not 100% as described above, the total incidence of arthritis was found to be nearly 100% if the swelling of small joints was taken into account. Judging from these results, the type of inheritance of the arthritis was considered to be incompletely dominant or recessive. By later experiments on the inheritance in a large scale, it was reasonably estimated that the genetic abnormality causing the natural onset of autoimmune arthritis is autosomal and recessive. The SKG mice are therefore maintained at present as homozygotes. Their incidence of arthritis is almost 100%, and the penetrance of the genetic abnormality in the homozygotes is considered to be almost 100% in the environment where they are currently maintained.

Example 2

Figure 1:
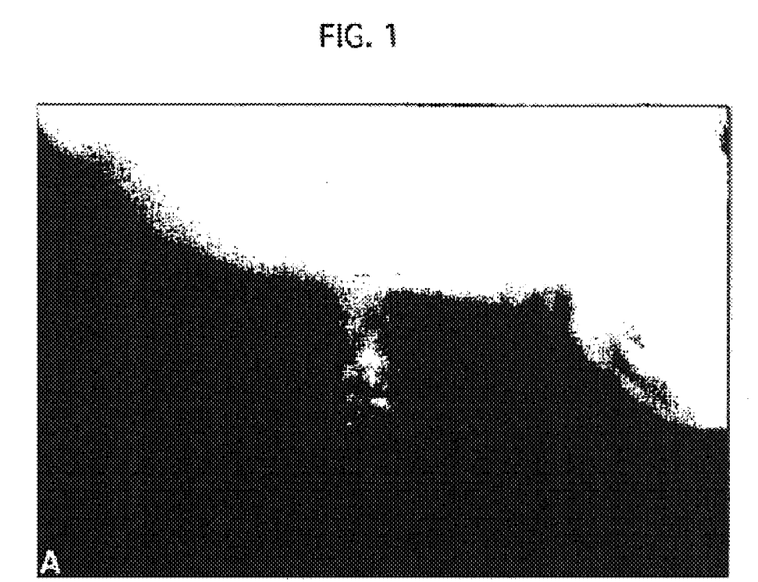
FIG. 1 is a photograph of a foreleg of a SKG mouse having developed arthritis.
Figure 2:
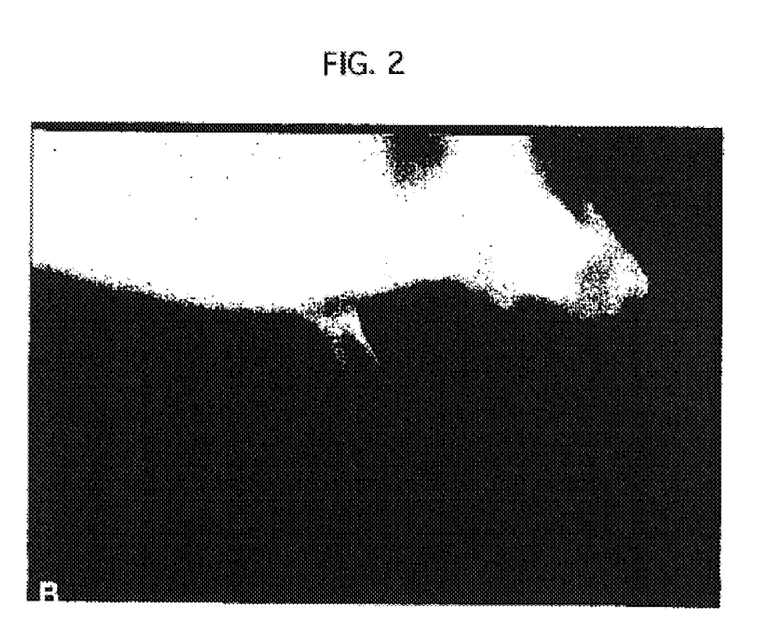
FIG. 2 is a photograph of a foreleg of a normal BALB/c mouse.
Figure 3:
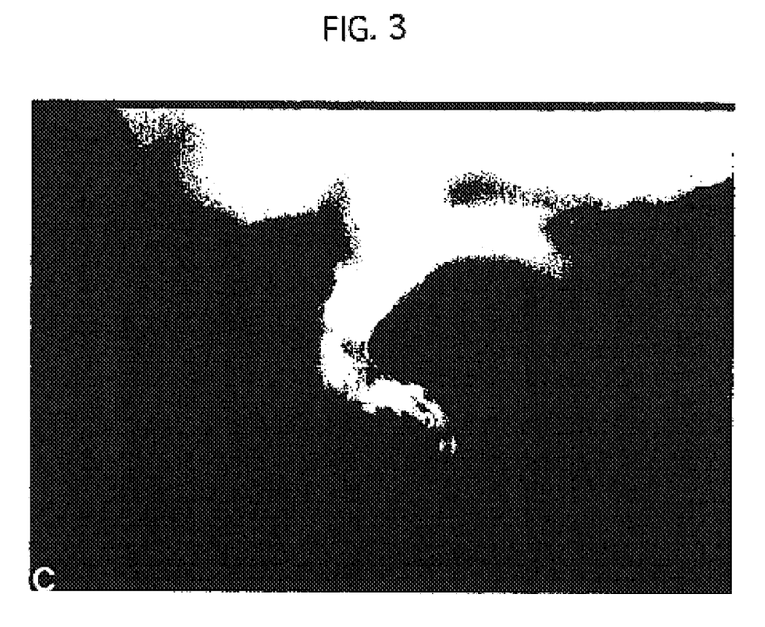
FIG. 3 is a photograph of a hind leg of a SKG mouse having developed arthritis.
Figure 4:
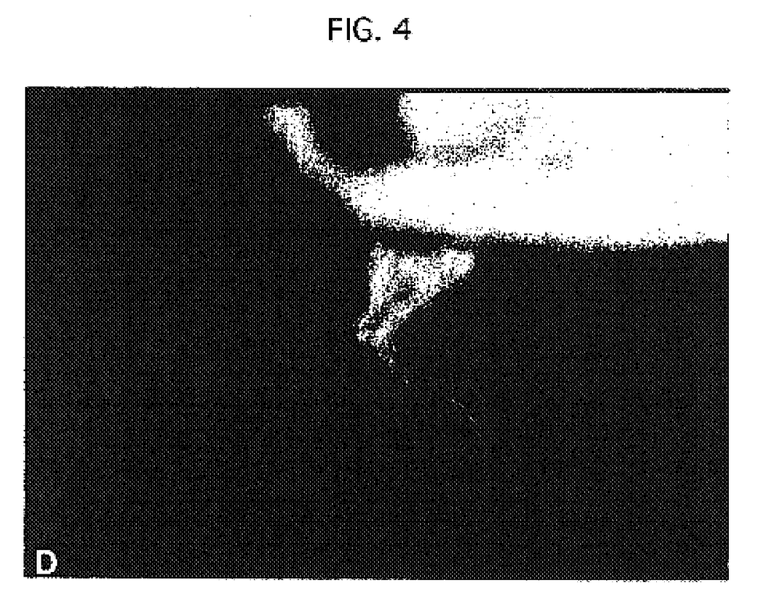
FIG. 4 is a photograph of a hind leg of a normal BALB/c mouse.

The forelegs and hind legs of a SKG mouse (6-month-old) having developed arthritis were observed with the naked eye. A photograph of a foreleg is shown in FIG. 1; and a photograph of a hind leg is shown in FIG. 3. As the control, photographs of a foreleg and hind leg of a normal mouse are shown in FIGS. 2 and 4, respectively.

As shown in FIGS. 1 and 3, swelling is observed in the joints of the forelegs and hind legs of the mouse having developed arthritis.

Example 3

Figure 5:
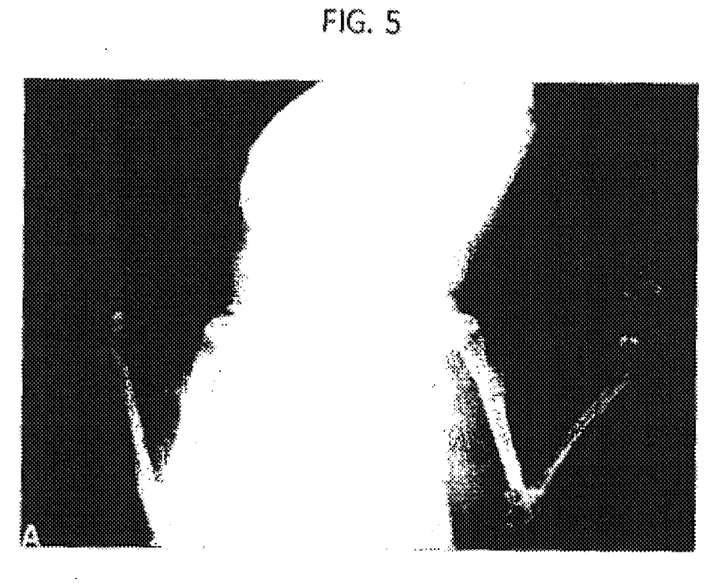
FIG. 5 is an X-ray photograph of forelegs of a SKG mouse having developed arthritis.
Figure 6:
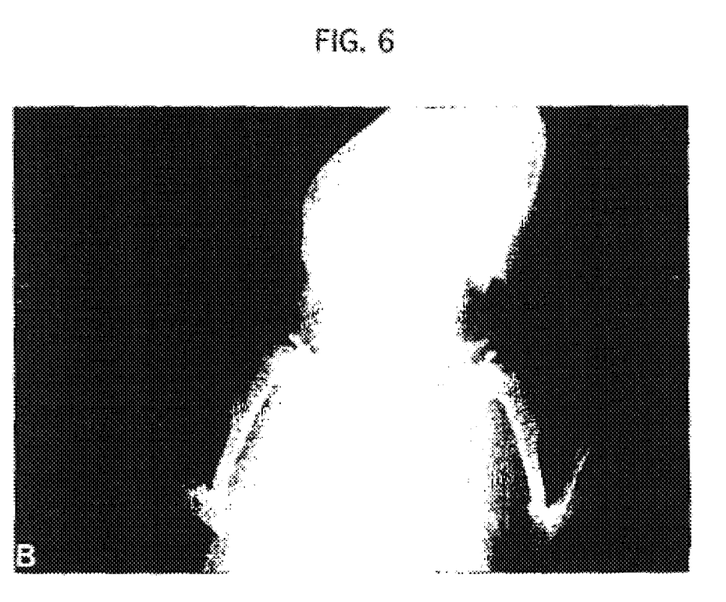
FIG. 6 is an X-ray photograph of forelegs of a normal BALB/c mouse.
Figure 7:
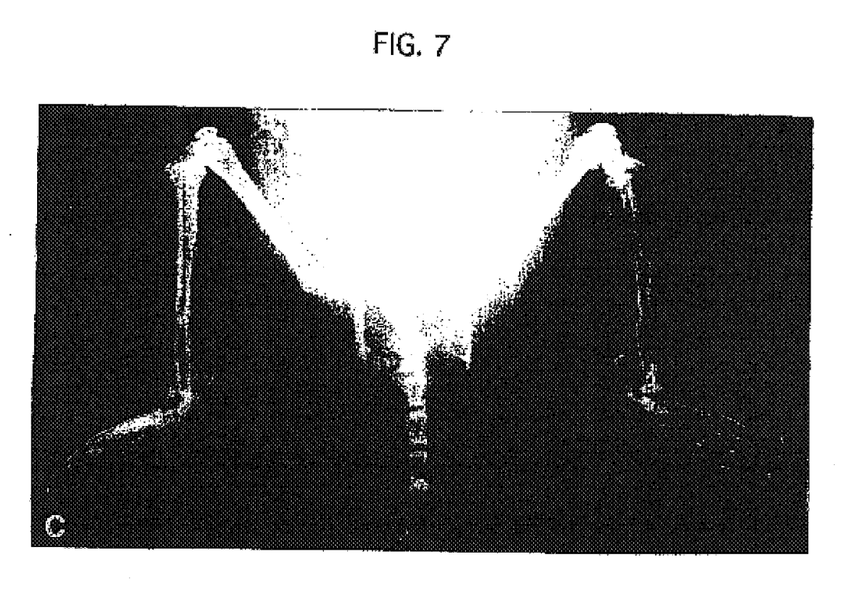
FIG. 7 is an X-ray photograph of hind legs of a SKG mouse having developed arthritis.
Figure 8:
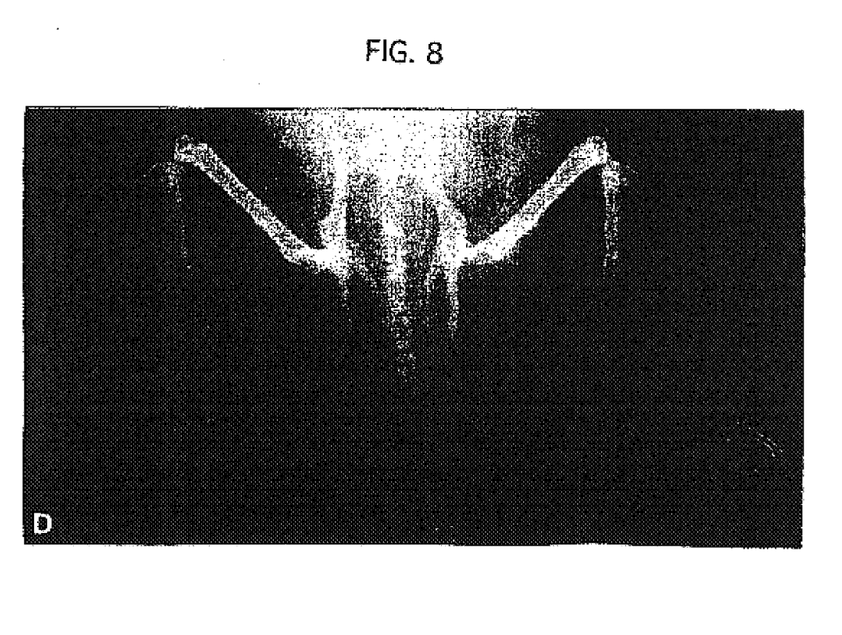
FIG. 8 is an X-ray photograph of hind legs of a normal BALB/c mouse.

X-ray photographs were taken of forelegs and hind legs of a SKG mouse (6-month-old) having developed arthritis. The photograph of the forelegs is shown in FIG. 5 and the photograph of the hind legs is shown in FIG. 7. As controls, photographs of forelegs and hind legs of a normal BACB/c mouse of the same age are shown in FIGS. 6 and 8, respectively.

As shown in FIGS. 5 and 7, the cartilage and bone are destroyed symmetrically in the large and small joints of the foreleg and hind leg.

Example 4

The joint of the hind leg of a SKG mouse (5-month-old) having developed arthritis was fixed in 10% formalin for 3 days, embedded in paraffin, cut into a thin section and stained with hematoxylin-eosin. A similar section was prepared from a normal mouse and stained.

Figure 10:
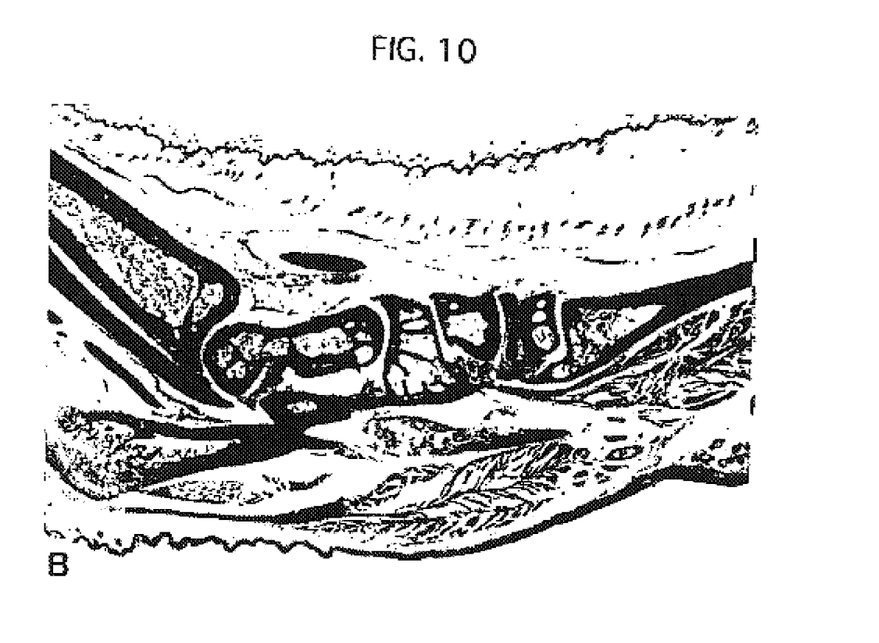
FIG. 10 is a microscopic photograph (magnification: ×40) of a section of the joint tissue prepared from a normal BALB/c mouse.
Figure 12:
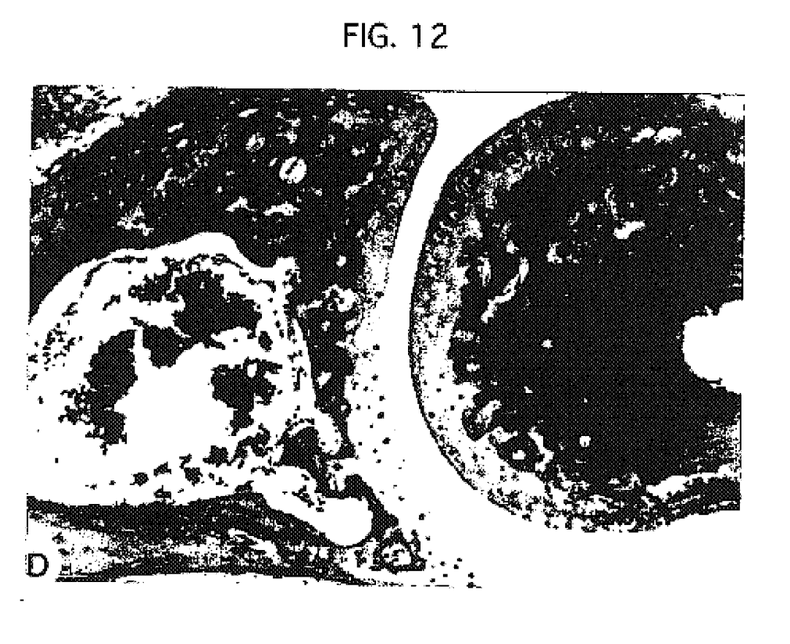
FIG. 12 is a microscopic photograph (magnification: ×400) of a section of the joint tissue prepared from a normal BALB/c mouse.

A microscopic photograph of a section of joint tissues from a SKG mouse having developed arthritis is shown in FIG. 9 (magnification: ×40) and FIG. 11 (magnification: ×400). A microscopic photograph of a similar section from a normal mouse is shown in FIG. 10 (magnification: ×40) and FIG. 12 (magnification: ×400).

FIG. 9 shows disappearance of the articular cavity, destruction of the cartilage and bone, and infiltration of inflammatory cells. FIG. 11 with further magnification indicates pannus formation, infiltration of inflammatory cells, and destruction of joint cartilage and bone.

Example 5

SKG mice (5- to 6-month-old) and normal BALB/c mice (5- to 6-month-old) were examined for the thickness of the left ankle joint. Fifteen mice each were examined. The result is shown in FIG. 13.

Figure 13:
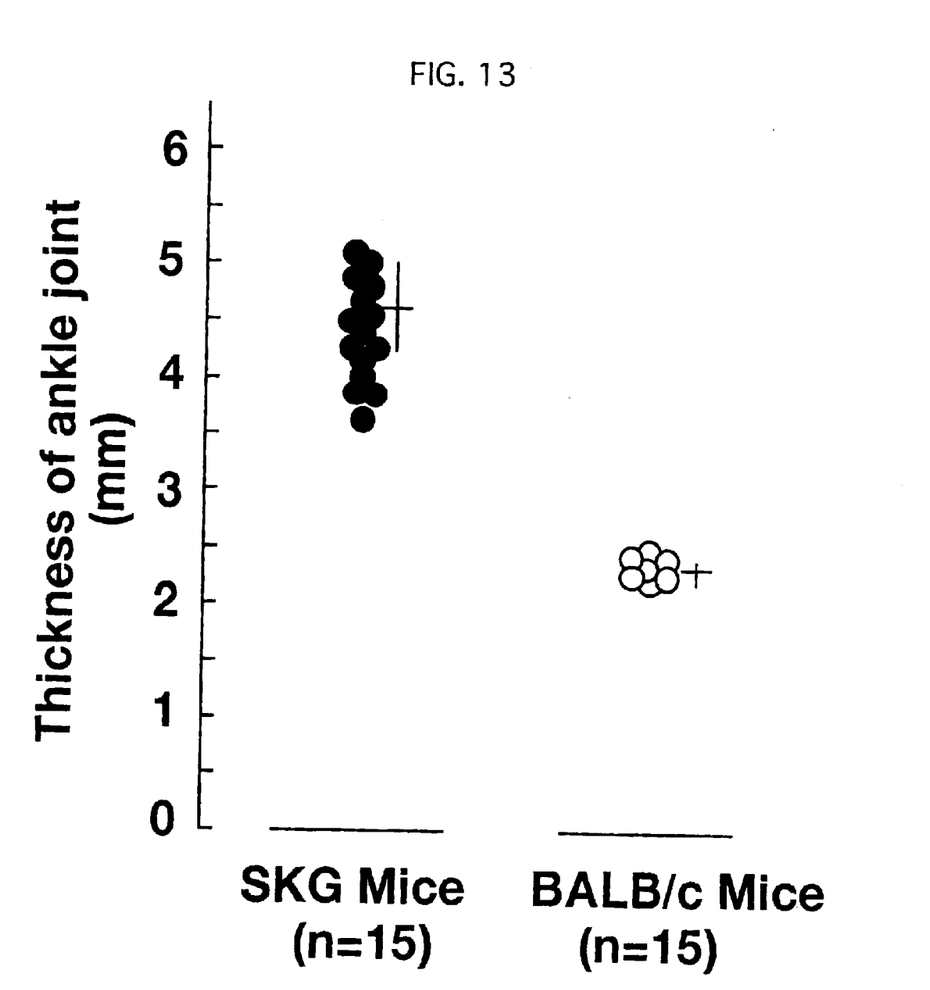
FIG. 13 is a graph showing the thickness of the left ankle joints of SKG mice at 56 months of age.

As shown in FIG. 13, the mice having developed arthritis had increased diameters of the ankle joint, as compared with those of the normal mice.

Example 6

SKG mice (5- to 6-month-old) and normal BALB/c mice (5- to 6-month-old) were examined by ELISA for the titer of IgM antibody (rheumatoid factor) against mouse immunoglobulin G (IgG). Fifteen animals each were examined. The result is shown in FIG. 14.

As shown in FIG. 14, the SKG mice having developed arthritis had significantly increased titers of rheumatoid factor, as compared with those of the normal BALB/c mice.

Example 7

SKG mice (5- to 6-month-old) and normal BALB/c mice (5- to 6-month-old) were examined by ELISA for the titer of circulating antibody against bovine type II collagen. Fifteen animals each were examined. The result is shown in FIG. 15.

As shown in FIG. 15, high titers of the autoantibody appear in the SKG mice with arthritis.

Example 8

SKG mice (5- to 6-month-old) and normal BALB/c mice (5- to 6-month-old) were examined for serum IgG levels by SRID (single radial immunodiffusion). Fifteen animals each were examined. The result is shown in FIG. 16.

As shown in FIG. 16, hypergammaglobulinemia is observed in the SKG mice having developed arthritis.

Example 9

Cell suspensions prepared from spleen and lymph node cells of the mice having developed arthritis were cultured in vitro for 3 days in the presence of concanavalin A, and the resulting $3 \times 10^7$ activated T cells were transferred intravenously to normal BALB/c nude mice (6-week-old). Two months after transfer, all the nude mice (7 animals) to which the cells had been transferred showed swelling of the joints of the hind legs. After 3 months, histological sections prepared as in Example 4 showed histological characteristics similar to those in FIGS. 9 and 11.

EFFECT OF THE INVENTION

The present invention relates to a mouse model with natural onset of the morbid conditions strikingly similar to those of human rheumatoid arthritis. This mouse is useful as an animal model of rheumatoid arthritis.

What is claimed is:

1. A mouse or a mouse strain that exhibits a phenotype comprising immunopathological characteristics indicative of autoimmune arthritis obtained from an embryo deposited as accession no. FERM BP-7790 with the International Patent Organism Depository.

* * * * *